United States Patent [19]

Sangokoya

[11] Patent Number: 5,157,137
[45] Date of Patent: Oct. 20, 1992

[54] METHOD OF MAKING GEL FREE ALKYLALUMINOXANE SOLUTIONS

[75] Inventor: Samuel A. Sangokoya, Baton Rouge, La.

[73] Assignee: Ethyl Corporation, Richmond, Va.

[21] Appl. No.: 736,416

[22] Filed: Jul. 26, 1991

[51] Int. Cl.$^5$ .............................................. C07F 5/06
[52] U.S. Cl. ..................................... 556/179; 556/181
[58] Field of Search ............................. 556/179, 181

[56] References Cited

U.S. PATENT DOCUMENTS

| | | | |
|---|---|---|---|
| 3,219,591 | 11/1965 | Vandenberg | 252/431 |
| 3,242,099 | 3/1966 | Manyik et al. | 252/429 |
| 3,300,458 | 1/1967 | Manyik et al. | 260/88.2 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,960,878 | 10/1990 | Crapo et al. | 556/179 |
| 4,968,827 | 11/1990 | Davis | 556/179 |
| 5,003,095 | 3/1991 | Beard | 556/179 |
| 5,015,749 | 5/1991 | Schmidt et al. | 556/179 |
| 5,041,583 | 8/1991 | Sangokoya | 556/179 |

FOREIGN PATENT DOCUMENTS 393358  3/1990  European Pat. Off. .

*Primary Examiner*—Jose G. Dees
*Assistant Examiner*—Porfirio Nazario
*Attorney, Agent, or Firm*—David M. Bunnell

[57] ABSTRACT

Clear, gel free solutions of alkylaluminoxane, such as methylaluminoxane, in an organic solvent, such as toluene, are provided by treating a solution of the alkylaluminoxane with an anhydrous salt and/or hydroxide of an alkali or alkaline earth metal and then removing the solids from the solution such as by filtration.

12 Claims, No Drawings

METHOD OF MAKING GEL FREE ALKYLALUMINOXANE SOLUTIONS

This invention relates generally to alkylaluminoxanes and more specifically to a method for providing clear, gel free organic solvent solutions of alkylaluminoxanes and especially methylaluminoxane by treating the solutions with certain alkali or alkaline earth metal compounds.

Vandenberg, U.S. Pat. No. 3,219,591 reported the catalytic activity of compounds formed by the reaction of trialkyl aluminum with limited amounts of water in the polymerization of epichlorohydrin and other oxiranes. Shortly thereafter, Manyik, et al. U.S. Pat. No. 3,242,099 reported the use of aluminoxanes, made by reacting 0.85-1.05 moles of water with hydrocarbyl aluminum compounds such as triisobutylaluminum, as co-catalysts with certain transition metal compounds in the polymerization of mono-unsaturated alpha-olefins; e.g. ethylene and propylene. Isobutylaluminoxane was also made by adding an equal mole quantity of water to a heptane solution of triisobutylaluminum.

Manyik, et al. U.S. Pat. No. 3,300,458 prepare alkylaluminoxanes by passing a hydrocarbon through water to form a wet hydrocarbon and mixing the wet hydrocarbon and an alkyl aluminum/hydrocarbon solution in a conduit.

Schoenthal, et al. U.S. Pat. No. 4,730,071 show the preparation of methylaluminoxane by dispersing water in toluene using an ultrasonic bath to cause the dispersion and then adding a toluene solution of trimethylaluminum to the dispersion. Schoenthal, et al. U.S. Pat. No. 4,730,072 is similar except it uses a high speed, high shear-inducing impeller to form the water dispersion.

Edwards, et al. U.S. Pat. N. 4,772,736 describe an aluminoxane process in which water is introduced below the surface of a solution of hydrocarbyl aluminum adjacent to a stirrer which serves to immediately disperse the water in the hydrocarbon solution.

A problem associated with free water addition to trimethylaluminum to produce methylaluminoxane solutions in organic solvents is that the solutions may contain gel and/or small particles which aggregate to form gel on standing. Even when the particles and/or gel are removed by filtration, additional gel can form in the solution after 2 or 3 weeks, especially when originally prepared dilute solutions are concentrated to contain higher aluminoxane contents which are convenient for storage, shipment and use. A treatment process has now been found that not only will remove such particles and gel from methylaluminoxane solutions but the solutions remain gel free.

BRIEF SUMMARY

In accordance with this invention there is provided a method of making a clear, gel free solution of alkylaluminoxane comprising treating an organic solvent solution of the alkylaluminoxane with an anhydrous salt and/or hydroxide of a metal selected from alkali and alkaline earth metals and then separating the solids from the solution.

DETAILED DESCRIPTION

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAL(C_2H_5)_2$. The compounds preferred for use in olefin polymerization catalysts usually contain about 4 to 20 of the repeating units:

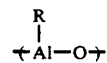

where R is $C_1$-$C_8$ alkyl and especially preferred are where R is methyl. Methylaluminoxanes (MAOs) normally have lower solubility in organic solvents than higher alkylaluminoxanes and the methylaluminoxane solutions tend to be cloudy or gelatinous due to the separation of particles and agglomerates. This problem is frequently encountered with MAO which has been prepared by adding free water, either neat or contained in a solvent, to a solution of trimethylaluminum as described, for example, in Manyik et al. U.S. Pat. No. 3,300,458 referred to above. According to such processes, the water-alkylaluminum reaction is carried out in an inert solvent. Any inert solvent can be used. The preferred solvents are aliphatic and aromatic hydrocarbons. Aromatic hydrocarbons are more preferred such as toluene, xylene, ethylbenzene, cumene, mesitylene and the like.

The process of the invention treats the cloudy or gelatinous MAO solutions, which contain from about 0.5 to 30 weight percent aluminum values, with an anhydrous salt and/or hydroxide of an alkali or alkaline earth metal in proportions of from about 0.01 to 0.1 moles of metal salt and/or hydroxide per mole of aluminum in the alkylaluminoxane.

The amount of treating compound is selected to remove the gel and particles while minimizing the loss of the desirable aluminum values.

Suitable anhydrous alkali and alkaline earth metal salts and hydroxides are those which are effective to remove the particulates and gel, but which are substantially inert with respect to the desirable aluminoxanes and any unreacted alkyl aluminum compounds remaining after formation of the aluminoxane.

Specific examples of useful treating compounds include anhydrous LiOH, LiBr, LiCl, NaOH, NaCl, NaBr, and the calcium, potassium, magnesium, barium analogs thereof.

The chemical nature of the particles and gel and the mechanism of removal is not known. The salts and/or hydroxides may be reacting with, encapsulating and/or agglomerating the particles, gel and potential gel forming materials in the solution so that they can be readily removed such as by filtering to separate the solids from the solution.

The treatment can be accomplished by adding the salt or hydroxide to the alkylaluminoxane solution with stirring for from about 1 to 4 hours at ambient temperatures (15°-30° C.). The time is not particularly critical and longer or shorter times, which are effective to transform the gels and particles to an easily filterable form, can be used. Higher or lower temperatures can also be used. Because the heavier metal compounds tend to be more reactive, especially with trimethylaluminum, the cleaning of methylaluminoxane with such compounds is preferable done at low temperatures.

After the treatment, the solids, including the treating compound, are conveniently removed from the solution by filtration but they can also be removed by any conventional liquid-solid separation technique such as by centrifugation and decanting the liquid. The treatment not only provides clear, gel free filtrates but the solutions are stable in that they remain gel free for extended periods of time.

The invention is further illustrated by, but is not intended to be limited to, the following examples in which the crude methylaluminoxane was prepared by direct water hydrolysis of trimethylaluminum.

EXAMPLE 1

A dilute solution of MAO (84.2 g, 0.92 wt % Al, 28.7 mmol Al) was filtered through a frit (15 μ). The filtrate was concentrated (4.6 wt. % Al) and analyzed for soluble aluminum content. It contained 79.7% of the original aluminum value (Sample 1A). Another sample (80.5 g, 0.92 wt. % Al, 27.4 mmol Al) was treated with 2.7 mmol LiOH. The mixture was stirred at room temperature for about 2 hours and then filtered. The filtrate contained 77.7% of the original aluminum value (Sample (1B).

On standing for about 4 weeks, both samples remained clear—no gel formation.

EXAMPLE 2

A solution of MAO (56.5 g, 5.04 wt % Al, 105.5 mmol Al) was filtered through a frit (15 μ). The filtrate was concentrated (6.5 wt. % Al) and found to contain 82.5% of the initial Al value (Sample 2A). From the same bottle, another sample (60.5 g, 5.04 wt. % Al, 113.0 mmol Al) was treated with anhydrous LiOH (11.3 mmol). The mixture was stirred at room temperature for about 2 hours and then filtered. The filtrate was concentrated (9.8 wt. % Al). The product contained 80.5% of the original Al content (Sample 2B).

After 4 weeks some precipitate started to form in sample 2A, but sample 2B, to which the LiOH treatment was applied remained clear and gel-free.

EXAMPLE 3

MAO (62.8 g, 4.14 wt. % Al, 96.3 mmol Al) was filtered through a frit (15 μ). After concentration (8.2 wt. % Al), the filtrate contained 91.8% of the initial Al value (Sample 3A). Another sample (75.4 g, 4.14 wt. % Al, 115.6 mmol Al) was treated with anhydrous LiOH (11.6 mmol) and then stirred at room temperature for about 3 hours. After filtration, the solution was concentrated (9.1 wt. % Al) and found to contain 90.9% of the initial aluminum value (Sample 3B).

Both samples were kept in the $N_2$-box. After 4 weeks, sample 3A had developed some solid-gel precipitate, while sample 3B remained clear and gel-free.

EXAMPLE 4

An aged, concentrated sample (15.86 wt. % Al) which had already turned gelatinous and could not be filtered was first diluted to 4.09 wt % Al. A sample of the diluted solution (69.3 g, 4.09 wt. % Al, 105.0 mmol Al) was filtered through a frit (15 μ). The filtrate was concentrated (12.4 wt % Al) and found to contain 73.3% of the original aluminum value (Sample 4A). Similarly, another diluted sample (58.4 g, 4.09 wt % Al, 88.5 mmol Al) was treated with anhydrous LiOH (8.8 mmol). The mixture was stirred at room temperature for about 3 hours. After filtration, the filtrate was concentrated (21 68 wt. % Al). The clear viscous product contained 75.1% of the original aluminum value (Sample 4B). After 4 weeks sample 4A contained some solid-gel precipitate while the clear viscous product of sample 4B remained gel free.

The foregoing examples are summarized in Table I below in which samples 1A, 2A, 3A and 4A are the untreated samples for comparison purposes.

TABLE I

Anhydrous LiOH Treatment[1] 2 of MAO Solutions

| Example | Al Values Treatment | Al Values Lost (Mol %) | Final, Filtered Conc. Sol (Wt. % Al) | Gel Formation After 4 Weeks |
|---|---|---|---|---|
| 1 | A | 20.1 | 4.6 | No |
|   | B | 22.3 | 6.5 | No |
| 2 | A | 17.9 | 6.5 | Yes |
|   | B | 19.5 | 9.8 | No |
| 3 | A | 8.2 | 8.9 | Yes |
|   | B | 9.1 | 10.1 | No |
| 4 | A | 26.7 | 12.4 | Yes |
|   | B | 24.9 | 21.68 | No |

[1]Approximately 10:1 (mol Al in MAO/mol LiOH) stirred at Room Temperature for about 2 hours.

The results demonstrate that the treatment process of the invention both removes gel and the treated solutions remain clear, in contrast gel formed in the solution which were only filtered.

What is claimed is:

1. A method of making a clear, gel free solution of alkylaluminoxane comprising treating an organic solvent solution of alkylaluminoxane with an anhydrous salt, an anhydrous hydroxide, or a mixture of an anhydrous salt and hydroxide of a metal selected from alkali and alkaline earth metals and then separating the solids from said solution.

2. The method of claim 1 wherein the alkylaluminoxane is methylaluminoxane.

3. The method of claim 2 wherein the solvent is an aromatic hydrocarbon.

4. The method of claim 3 wherein the solvent is toluene.

5. The method of claim 2 wherein the metal is lithium.

6. The method of claim 5 wherein anhydrous lithium hydroxide is used in the process.

7. The method of claim 5 wherein anhydrous lithium bromide is used in the process.

8. The method of claim 1 wherein the solids are separated by filtering the solution.

9. A method of removing gel from a hydrocarbon solvent solution of methylaluminoxane comprising mixing an anhydrous salt, an anhydrous hydroxide, or a mixture of an anhydrous salt and hydroxide of an alkali metal or an alkali earth metal with said solution containing said gel and then separating the solids from said solution.

10. The method of claim 9 wherein said solvent is an aromatic hydrocarbon and said metal is an alkali metal.

11. The method of claim 10 wherein said solvent is toluene and said metal is lithium.

12. The method of claim 9 wherein anhydrous lithium hydroxide is mixed with the solution and the solids are separated from the solution by filtering the solution.

* * * * *